United States Patent [19]

Balaban et al.

[11] Patent Number: 5,393,547
[45] Date of Patent: Feb. 28, 1995

[54] INACTIVATION OF ENZYMES IN FOODS WITH PRESSURIZED $CO_2$

[75] Inventors: Murat O. Balaban; Maurice R. Marshall, both of Gainesville, Fla.; Louise Wicker, Comer, Ga.

[73] Assignee: University of Florida, Gainesville, Fla.

[21] Appl. No.: 452,496

[22] Filed: Dec. 19, 1989

Related U.S. Application Data

[63] Continuation-in-part of Ser. No. 243,275, Sep. 12, 1988, abandoned.

[51] Int. Cl.⁶ .......................... A23B 4/12; A23C 3/08; A23L 2/18
[52] U.S. Cl. .............................. 426/330; 426/330.5; 426/335; 426/532
[58] Field of Search ..................... 426/330, 330.5, 335, 426/532, 312, 315

[56] References Cited

U.S. PATENT DOCUMENTS 3,442,660 5/1969 Shank .................................. 426/312
3,597,235 8/1971 Kramer .............................. 426/335

OTHER PUBLICATIONS

Fite et al, "The Effect of Carbon Dioxide Upon the pH and Certain Nitrogen Fractions of the Sugar Beet Plant", 1935 pp. 643–655.
Chemical Abstracts 93: 148368s p. 566, 1980.
Chemical Abstracts 105: 113696m p. 559, 1986.
Abstract; 1987 Institute of Food Technologists Annual Meeting/Las Vegas, Jun. 16–19, 1987.
Owusu-Yaw, et al, *J. Food Sci.*, vol. 53, "Low pH Inactivation of Pectinesterase in Single Strength Orange Juice," pp. 504–507 (1987).

*Primary Examiner*—Arthur L. Corbin
*Attorney, Agent, or Firm*—Kerkam, Stowell, Kondracki & Clarke

[57] ABSTRACT

A method for inactivating enzymes in food products comprising exposing the food to pressurized $CO_2$ to produce a carbonic acid solution therein having a pH sufficiently low to irreversibly inactivate the enzymes.

6 Claims, 2 Drawing Sheets

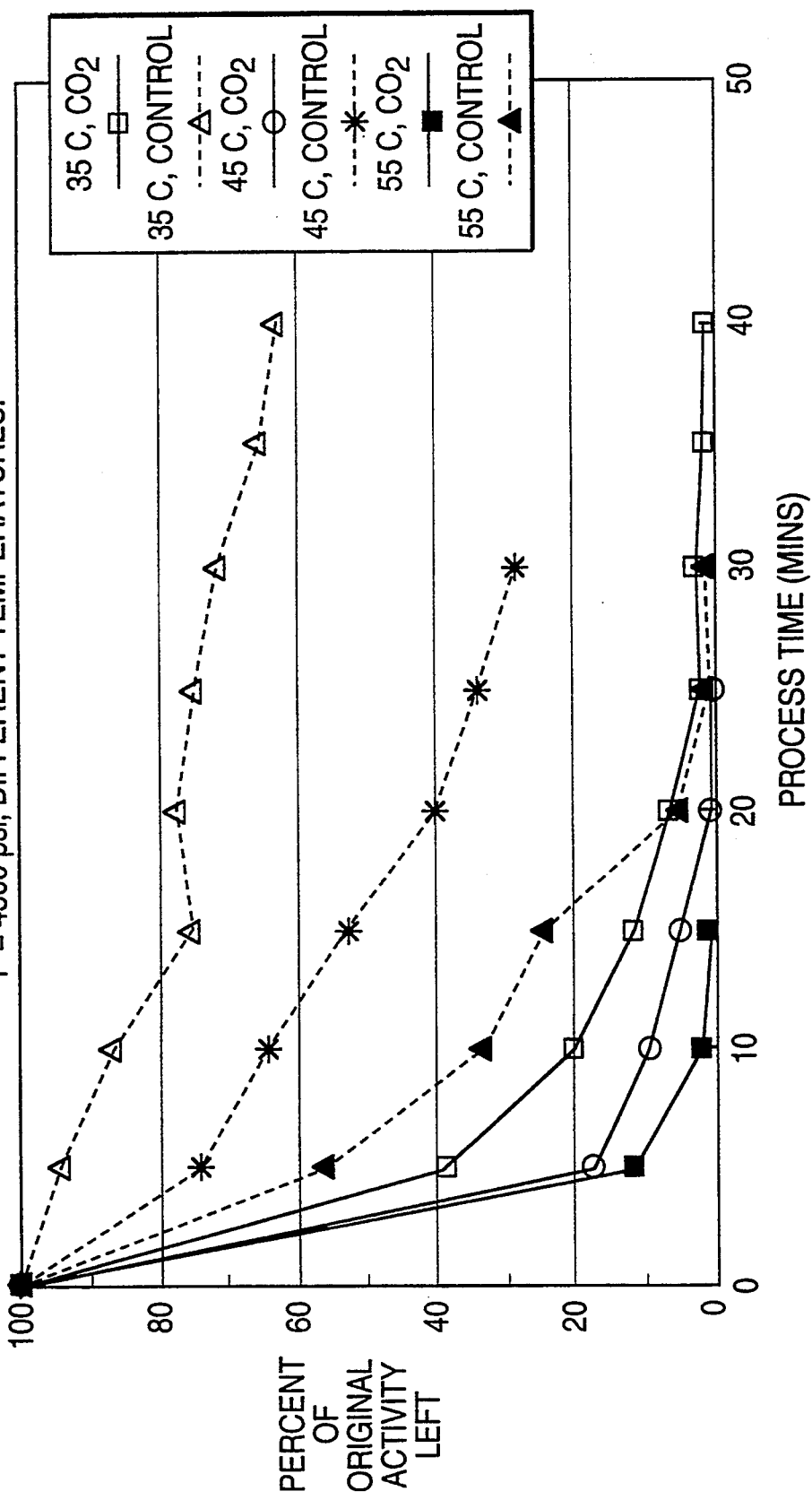

INACTIVATION OF ENZYMES IN FOODS WITH PRESSURIZED $CO_2$

RELATED APPLICATIONS

This is a continuation-in-part of application Ser. No. 243,275, filed Sep. 12, 1988, now abandoned.

BACKGROUND OF THE INVENTION

1. Field of the Invention

The present invention relates to the inactivation of undesirable enzymes.

2. The Prior Art

It is well known that certain enzymes in food products contribute to their spoilage during storage over long periods of time.

The traditional method to inactivate these undesirable enzymes is to expose the food product to elevated temperatures which will normally destroy such enzymes. The application of heat, however, has a deleterious effect on the quality, feel or "freshness" of the food product. Thus, the elevated temperatures are not specific to enzymes but also degrade other components of the food which contribute to desirable qualities in the food product.

It has been reported in the literature [Owusu-Yaw et al, J. Food Sci., Vol. 53 (2), pp. 504–507 (1988); reported in abstract form at IFT Annual Meeting, Jun. 16–19, 1987] that the enzyme, pectinesterase (PE) can be irreversibly inactivated after addition to orange juice by lowering the pH of the juice product. This is achieved by the addition of hydrochloric acid or ion exchange resin. The addition of chemicals, however, to food products is viewed by the general public as undesirable and there exist many regulations governing the addition of such chemicals to foods. The use of ion exchange resins suffers from the additional disadvantage that it removes or destroys many flavor attributes of the food product viewed as desirable by the consumer.

It is an object of the present invention to provide a system for inactivating deleterious enzymes in foods which reduces or eliminates the above-noted disadvantages.

SUMMARY OF THE INVENTION

This and other objects are realized by the present invention which provides a method for inactivating at least one undesirable enzyme in a food product containing an aqueous phase comprising exposing the food product to an atmosphere having a partial pressure of $CO_2$, and for a time, sufficient to result in a dissolution of sufficient $CO_2$ in the aqueous phase of the food product to produce a carbonic acid solution having a pH sufficiently low to irreversibly inactivate the enzyme.

Additional embodiments of the invention comprise the food products produced according to the above-described method.

BRIEF DESCRIPTION OF THE DRAWINGS

FIGS. 1 and 2 graphically depict the results of the methods described in Examples 2 and 3, below, respectively.

DESCRIPTION OF THE INVENTION

Figure 2A:
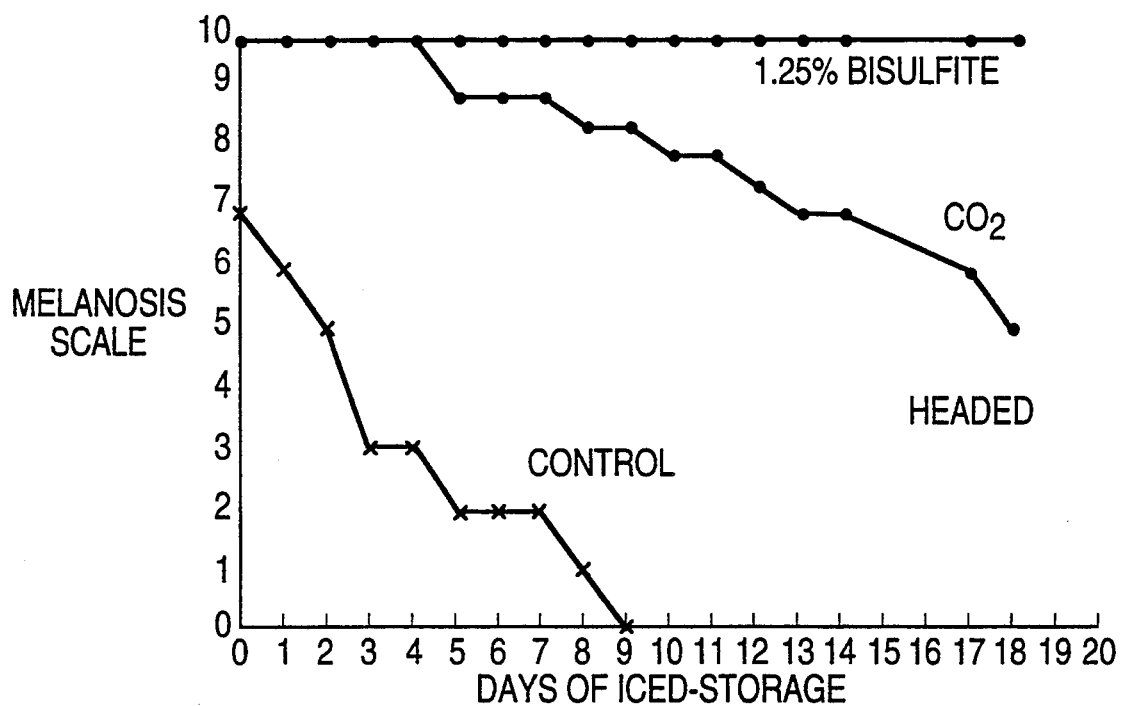

The method according to the present invention results in an irreversible inactivation of deleterious enzyme(s) in food products without the disadvantages attendant conventional methods heretofore employed for this purpose. Thus, the carbon dioxide dissolves in the aqueous phase of the food product resulting in the formation of carbonic acid. Sufficient $CO_2$ is dissolved in the aqueous part of the food to create a carbonic acid solution having a pH sufficiently low to inactivate the enzyme(s) After the treatment, which inactivates the enzyme(s) irreversibly, the $CO_2$ partial pressure is reduced and carbonic acid is decomposed into water and gaseous carbon dioxide which bubbles out of the aqueous phase.

It can be seen that the method of the invention lowers the pH of the food product, inactivates the enzyme(s) and then restores the pH to its original value without the net removal or addition of any component from or to the food. In addition, the feel, freshness and consumer-appeal quality of the food product is maintained.

The method of the invention is applicable to any food product having an aqueous phase containing, or being surrounded by a sufficient amount of an aqueous phase to dissolve sufficient $CO_2$ to inactivate the target enzyme(s). Suitable such foods include liquid foods such as fruit and vegetable juices, milk, beverages, etc.; semi-solid foods, e.g., fruit and vegetable purees, etc.; solid food surfaces, e.g., shrimp, seafoods, meats, fruit slices, etc.

While it is preferred to dissolve the $CO_2$ in the aqueous phase of the food product utilizing a substantially pure $CO_2$ atmosphere, it will be understood by those skilled in the art that any atmosphere containing a $CO_2$ partial pressure sufficiently high to dissolve enough carbon dioxide to form the requisite carbonic acid solution may be utilized. Thus, mixtures of carbon dioxide with nitrogen, helium, air, sulfur dioxide, carbon monoxide, chlorine, argon, etc., can be utilized in the practice of the present invention.

The pH to which the solution must be lowered will depend, of course, upon the enzyme(s) to be inactivated. The inactivation pH values of the various enzymes are either known or can easily be determined by conducting routine experimentation.

The partial pressure of $CO_2$ necessary to dissolve sufficient $CO_2$ into the system to result in the requisite pH will depend upon the electrolytes and other materials dissolved in the aqueous phase from the food products as well as the ambient temperature, etc. The skilled artisan, having been exposed to the principles described herein, is capable of determining the $CO_2$ partial pressure necessary for any given application without the exercise of inventive faculties. Generally, however, $CO_2$ partial pressures of from about 0.5 atm to about 1000 atm at temperatures in the range of from 20° C. to about 200° C. will be sufficient to dissolve sufficient $CO_2$ in any of the above-noted food products to lower the pH sufficiently to inactivate most deleterious enzymes.

Any conventional gas pressure treating system can be utilized in the practice of the invention. Typically, any apparatus having a size sufficient to hold the food product to be treated and having a gas inlet and outlet means as well as means to induce elevated pressures and apply elevated temperatures can be employed.

The carbon dioxide is allowed to remain dissolved in the aqueous phase for a time sufficient to inactivate the enzymes. The time required will depend in each instance upon the nature and the environment of the enzyme(s) to be inactivated and is easily determined in each case.

The method of the invention can be applied in either a batch mode or in a continuous flow mode. In the batch mode of operation, the food is placed in a pressure vessel where the temperature and pressure can be controlled. Pure $CO_2$ is preferably introduced under pressure and at an appropriate temperature. The pressures are maintained for a time interval sufficiently long to inactivate the enzyme(s). The pressure is then reduced and the $CO_2$ gas is separated from the food. Generally, release of the pressure will result in evolution of most of the dissolved $CO_2$. Additional $CO_2$ may be removed by slightly warming the food or subjecting it to a negative pressure, or to mechanical treatment.

In the continuous flow mode, the food is brought to the desired pressure with optional heating or cooling to maintain the desired temperature. Gaseous $CO_2$ is introduced at high pressure at the beginning of the holding section such as a pipe, tube, vessel, etc. The flowrate through the vessel is maintained at a rate sufficient to allow enough $CO_2$ to dissolve in the food to inactivate the enzymes. After inactivation, the food flows to a sect ion where the pressure is reduced and released $CO_2$ is recycled to the first stage.

Any drying effect of the $CO_2$ on the food product can be negated by saturating the treating gas with water vapor.

A beneficial side effect of the method of the present invention when applied to fruit juices, e.g., orange juice, is that the desirable "cloud" of the juice is enhanced by the $CO_2$ treatment. The precise mechanism by which the cloud of the juice is enhanced is not entirely understood; however, it has been determined that juices having virtually no cloud have their cloud effect raised by the method of the present invention to desirable levels acceptable in the marketplace. In addition, it has been found that the enhanced cloud produced by the method of the invention is much more stable to deterioration than the cloud produced according to conventional techniques.

The invention is illustrated by the following non-limiting examples.

EXAMPLE 1

The activity of pectinesterase enzyme (found in, e.g., orange juice, pH 3.5 to 4.0) is reduced at a pH value of about 2.6. An experiment was performed to determine that orange juice, subjected to a $CO_2$ pressure of about 4500 psi had its pH lowered to below 2.6. Samples of orange juice were subjected to $CO_2$ atmospheres having a pressure of 4500 psi for 120 minutes. Identical samples of orange juice were subjected to the identical gas at atmospheric pressure for the same amount of time. Juice samples treated with high pressure $CO_2$ showed no enzyme activity whereas in the controls there remained extensive activity.

EXAMPLE 2

It was determined that polyphenoloxidase can be inactivated at a pH of about 2.5.

The procedure of Example 1 was repeated utilizing apple juice. The samples subjected to high pressure $CO_2$ showed no enzyme activity after 60 minutes. The controls still showed considerable enzyme activity after the same amount of time.

The graph set forth in FIG. 1 depicts the results of Example 2.

EXAMPLE 3

Pink shrimp (Penaeus spp.) not treated with bisulfite were divided into two groups. One group of shrimp with heads intact was used for melanosis studies The other group comprised shrimp with heads removed for quality and texture determination. Each group was sub-divided into three treatment groups: control, bisulfite treatment and $CO_2$ treatment.

Of the headless shrimp, the control group was dipped in water and placed on ice. The bisulfite group was treated with 1.25% sodium bisulfite for 1 min. and placed on ice. The third sub-group was placed in a pressure vessel with an equal amount of water. The vessel was pressurized to 4500 psi at 96° F. with carbon dioxide for 2 hours. The vessel was de-pressurized and the shrimp removed, placed in sterile bags and put on ice. Samples were taken at 0, 5, 10 and 14 days of storage and examined for melanosis. Each sample was cooked after examination and evaluated for texture and odor.

The shrimp with heads intact were treated similarly to the headless shrimp, except that both the control and sulfite-treated samples were placed aseptically in sterile bags and put in a water bath at the same temperature employed in the $CO_2$ treatment, the shrimp were placed in sterile bags and all samples placed on ice.

The $CO_2$ treated headless shrimp exhibited a pleasant reddish-orange appearance at day 0 after treatment. This appearance was not present in the control and bisulfite sub-groups.

At day 3, the $CO_2$ treated headless samples were equal to if not superior in appearance than the bisulfite treated samples. The control group exhibited severe melanosis and would be unmarketable.

Both cooked and uncooked $CO_2$ and bisulfite samples were comparable in appearance and texture at day 5. Both were far superior to the control group. No objectionable odors were detected in any of the sub-groups.

At day 10, among the heads-intact samples, the $CO_2$ group developed melanosis only at the heads; there was no darkening of the tails. They were still far superior to the controls.

At day 10, the $CO_2$ treated heads-off shrimp were far superior to the bisulfite and control samples. Placing of the samples directly on ice resulted in a washing-off of some of the bisulfite. Cooked samples were tasted. There was some unobjectional softening of the exterior muscle in the $CO_2$ group compared to the bisulfite samples. Only the controls exhibited a strong smell of ammonia.

At day 14, the $CO_2$ treated samples exhibited a better appearance than the bisulfited and control samples. At this point, the bisulfited samples are considered borderline with respect to the onset of melanosis. The cooked $CO_2$ samples had no discernible odor of ammonia whereas both the bisulfited and control samples had a strong odor of ammonia. The exterior softness of the $CO_2$ shrimp was similar to that at day 10.

Figure 2B:
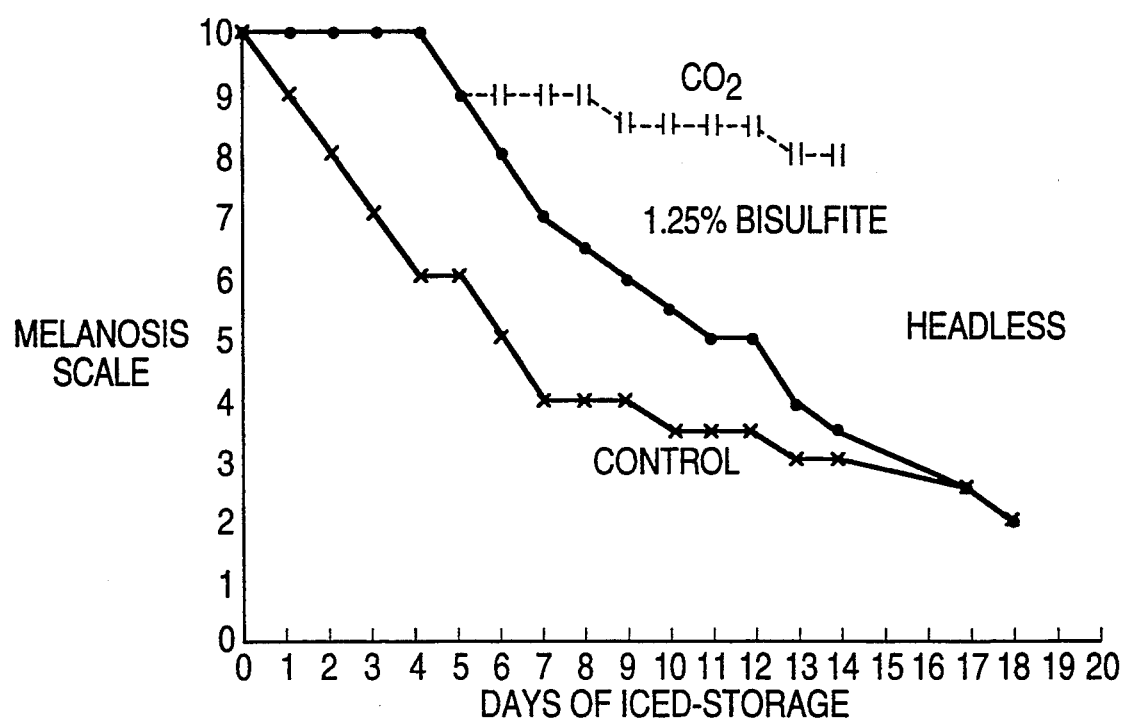

The above results are depicted in the graph in FIG. 2. The melanosis rating scale is based on occurrence of blackening due to melanosis: A score of 10–9, no melanosis; 8–7, insignificant melanosis; 6–5, noticeable melanosis; 4–3, distinct melanosis (unacceptable); below 2, severe melanosis (unacceptable).

EXAMPLE 4

A study was undertaken to investigate the bactericidal effect of $CO_2$ treatment. It was demonstrated that about 35-45% of the spiked *Listeria monocytogenes* on shrimp samples was killed at 820 psi $CO_2$, at room temperature for 2 hours. When the pressure was increased to 2000 psi $CO_2$, over 98% of the spiked bacteria was killed after 2 hours in five separate experiments (killing efficiency: 98 5%, 99% 98.4%, >99.8% and >99.7%).

In all these studies, the shrimp samples with shell on were dipped for 2 min. in *L. monocytogenes* suspension in distilled water. After the excessive liquid was dripped off, the shrimp was put in test tubes and subjected to $CO_2$ treatment as described, or incubated at 35° C. for 2 hrs in an incubator as control. The bacterial number in the suspension was determined by surface plating on trypticase soy agar of the serially diluted suspension in Butterfield's buffer. The treated and the two control samples (shrimp sample at time 0 and that incubated at 35° C.) were homogenized in 1:10 dilution with Butterfield's buffer in a sterile Waring blender for 2 min at 8000 rpm. Aliquots of the homogenates were removed, serially diluted and surface plated on trypitcase agar. After incubation for 24 hrs at 37° C., the bacterial number was compared among the treated and control groups and the percent of killing was determined.

These indicate that the $CO_2$ treatment markedly improves the quality and shelf-life of the shrimp. Since the melanosis effect, and the microbial contamination are largely surface phenomena, the size of the sample will not affect the treatment.

We claim:

1. A method for inactivating at least one undesirable enzyme in a food product containing at least one such undesirable enzyme which is sensitive to inactivation at a lowered pH value and an aqueous phase comprising exposing said food product to an atmosphere having a partial pressure of $CO_2$ of from about 0.5 atm. to about 1,000 atm. at a temperature of from about 0° C. to about 200° C. for a time sufficient to result in dissolution of sufficient $CO_2$ in the aqueous phase of said food product to produce a carbonic acid solution having a pH sufficiently low to irreversibly inactivate said enzyme.

2. The method of claim 1 including the step of removing dissolved $CO_2$ from said food product after inactivation of said at least one enzyme.

3. The method of claim 2 wherein said dissolved $CO_2$ is removed from said food product by reducing the partial pressure of $CO_2$ in said atmosphere.

4. The method of claim 2 or 3 wherein said dissolved $CO_2$ is removed from said food product by elevating the temperature of said food product.

5. The method of claim 2 where sufficient dissolved $CO_2$ is removed to restore said food product to substantially its pH value before exposure to said $CO_2$ containing atmosphere.

6. The method of claim 1 wherein said atmosphere is substantially pure $CO_2$.

* * * * *